United States Patent [19]

Cherpeck

[11] Patent Number: 5,569,310
[45] Date of Patent: Oct. 29, 1996

[54] POLY(OXYALKYLENE) HYDROXYAROMATIC ETHERS AND FUEL COMPOSITIONS CONTAINING THE SAME

[75] Inventor: Richard E. Cherpeck, Cotati, Calif.

[73] Assignee: Chevron Chemical Company, San Ramon, Calif.

[21] Appl. No.: 992,953

[22] Filed: Dec. 18, 1992

[51] Int. Cl.$^6$ .................................................. C10L 1/18
[52] U.S. Cl. ................................. 44/442; 44/400; 44/443
[58] Field of Search ...................... 568/607, 608, 568/609, 610, 611, 606; 560/103, 129, 144, 109, 112; 44/443, 447, 448, 449, 450, 442, 400

[56] References Cited

U.S. PATENT DOCUMENTS

| | | | |
|---|---|---|---|
| 2,213,477 | 9/1940 | Steindorff et al. | 568/606 |
| 2,984,553 | 5/1961 | Andress | 44/443 |
| 3,123,561 | 3/1964 | Rue | 568/609 |
| 3,849,085 | 11/1974 | Kreuz et al. | 44/78 |
| 4,134,846 | 1/1979 | Machleder et al. | 252/51.5 |
| 4,191,537 | 3/1980 | Lewis et al. | 44/71 |
| 4,298,352 | 11/1981 | Blysing | 44/443 |
| 4,384,872 | 5/1983 | Kester et al. | 44/443 |
| 4,915,875 | 4/1990 | Diephouse et al. | 568/607 |
| 4,952,732 | 8/1990 | Speranza et al. | 564/390 |
| 5,024,678 | 6/1991 | Mertens-Gottselig et al. | 44/400 |

FOREIGN PATENT DOCUMENTS

| | | | |
|---|---|---|---|
| 0708193 | 4/1954 | United Kingdom | 44/447 |

OTHER PUBLICATIONS

CA 107(14) 124471b of JP62 06,249 13 Jan. 1987.
RN 110327-78-1 (date unknown).

*Primary Examiner*—Jerry D. Johnson
*Attorney, Agent, or Firm*—C. J. Caroli

[57] ABSTRACT

Poly(oxyalkylene) hydroxyaromatic ethers having the formula:

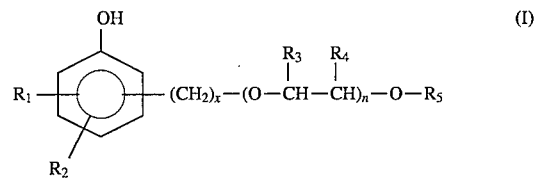

or a fuel-soluble salt thereof; where $R_1$ and $R_2$ are each independently hydrogen, hydroxy, lower alkyl having 1 to 6 carbon atoms, or lower alkoxy having 1 to 6 carbon atoms; $R_3$ and $R_4$ are each independently hydrogen or lower alkyl having 1 to 6 carbon atoms; $R_5$ is hydrogen, alkyl having 1 to 30 carbon atoms, phenyl, aralkyl or alkaryl having 7 to 36 carbon atoms, or an acyl group of the formula:

$$\begin{matrix} O \\ \| \\ -C-R_6 \end{matrix}$$

where $R_6$ is alkyl having 1 to 30 carbon atoms, phenyl, or aralkyl or alkaryl having 7 to 36 carbon atoms; n is an integer from 5 to 100; and x is an integer from 0 to 10.

The poly(oxyalkylene) hydroxyaromatic ethers of formula I are useful as fuel additives for the prevention and control of engine deposits.

15 Claims, No Drawings

POLY(OXYALKYLENE) HYDROXYAROMATIC ETHERS AND FUEL COMPOSITIONS CONTAINING THE SAME

BACKGROUND OF THE INVENTION

1. Field of the Invention

This invention relates to novel hydroxyaromatic compounds. More particularly, this invention relates to novel poly(oxyalkylene) hydroxyaromatic ethers and their use in fuel compositions to prevent and control engine deposits.

2. Description of the Related Art

It is well known that automobile engines tend to form deposits on the surface of engine components, such as carburetor ports, throttle bodies, fuel injectors, intake ports and intake valves, due to the oxidation and polymerization of hydrocarbon fuel. These deposits, even when present in relatively minor amounts, often cause noticeable driveability problems, such as stalling and poor acceleration. Moreover, engine deposits can significantly increase an automobile's fuel consumption and production of exhaust pollutants. Therefore, the development of effective fuel detergents or "deposit control" additives to prevent or control such deposits is of considerable importance and numerous such materials are known in the art.

For example, aliphatic hydrocarbon-substituted phenols are known to reduce engine deposits when used in fuel compositions. U.S. Pat. No. 3,849,085, issued Nov. 19, 1974 to Kreuz et al., discloses a motor fuel composition comprising a mixture of hydrocarbons in the gasoline boiling range containing about 0.01 to 0.25 volume percent of a high molecular weight aliphatic hydrocarbon-substituted phenol in which the aliphatic hydrocarbon radical has an average molecular weight in the range of about 500 to 3,500. This patent teaches that gasoline compositions containing minor amount of an aliphatic hydrocarbon-substituted phenol not only prevent or inhibit the formation of intake valve and port deposits in a gasoline engine, but also enhance the performance of the fuel composition in engines designed to operate at higher operating temperatures with a minimum of decomposition and deposit formation in the manifold of the engine.

Similarly, U.S. Pat. No. 4,134,846, issued Jan. 16, 1979 to Machleder et al., discloses a fuel additive composition comprising a mixture of (1) the reaction product of an aliphatic hydrocarbon-substituted phenol, epichlorohydrin and a primary or secondary mono- or polyamine, and (2) a polyalkylene phenol. This patent teaches that such compositions show excellent carburetor, induction system and combustion chamber detergency and, in addition, provide effective rust inhibition when used in hydrocarbon fuels at low concentrations.

Fuel additives containing a poly(oxyalkylene) moiety are also known in the art. For example, U.S. Pat. No. 4,191,537, issued Mar. 4, 1980 to R. A. Lewis et al., discloses a fuel composition comprising a major portion of hydrocarbons boiling in the gasoline range and from 30 to 2000 ppm of a hydrocarbyl poly(oxyalkylene) aminocarbamate having a molecular weight from about 600 to 10,000, and at least one basic nitrogen atom. The hydrocarbyl poly(oxyalkylene) moiety is composed of oxyalkylene units selected from 2 to 5 carbon oxyalkylene units. These fuel compositions are taught to maintain the cleanliness of intake systems without contributing to combustion chamber deposits.

Aromatic compounds containing a poly(oxyalkylene) moiety are also known in the art. For example, the above-mentioned U.S. Pat. No. 4,191,537, discloses alkylphenyl poly(oxyalkylene) polymers which are useful as intermediates in the preparation of alkylphenyl poly(oxyalkylene) aminocarbamates.

Additionally, hydroxyaromatic compounds containing a poly(oxyalkylene) moiety are known in the art. For example, U.S. Pat. No. 4,952,732, issued Aug. 28, 1990 to G. P. Speranza et al., discloses Mannich condensates prepared from a phenol, formaldehyde and an alkylamine containing propoxy groups and, optionally, ethoxy groups. These Mannich condensates are taught to be useful as corrosion inhibitors, water repellent agents, paint adhesion promotors, and also as intermediates for preparing surfactants, and pololys finding use in the manufacture of polyurethane foam.

It has now been discovered that certain hydroxyaromatic ethers having a poly(oxyalkylene) "tail" provide excellent control of engine deposits, especially intake valve deposits, when employed as fuel additives in fuel compositions. Moreover, these poly(oxyalkylene) hydroxyaromatic ethers have been found to produce fewer combustion chamber deposits than known aliphatic hydrocarbon-substituted phenolic fuel additives.

SUMMARY OF THE INVENTION

The present invention provides novel poly(oxyalkylene) hydroxyaromatic ethers which are useful as fuel additives for the prevention and control of engine deposits, particularly intake valve deposits.

The poly(oxyalkylene) hydroxyaromatic ethers of the present invention have the formula:

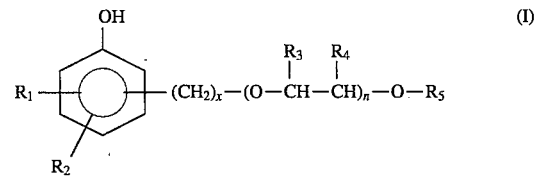

(I)

or a fuel-soluble salt thereof; wherein $R_1$ and $R_2$ are each independently hydrogen, hydroxy, lower alkyl having 1 to 6 carbon atoms, or lower alkoxy having 1 to 6 carbon atoms; $R_3$ and $R_4$ are each independently hydrogen or lower alkyl having 1 to 6 carbon atoms; is hydrogen, alkyl having 1 to 30 carbon atoms, phenyl, aralkyl or alkaryl having 7 to 36 carbon atoms, or an acyl group of the formula:

wherein $R_6$ is alkyl having 1 to 30 carbon atoms, phenyl, or aralkyl or alkaryl having 7 to 36 carbon atoms; n is an integer from 5 to 100; and x is an integer from 0 to 10.

The present invention further provides a fuel composition comprising a major amount of hydrocarbons boiling in the gasoline or diesel range and an effective deposit-controlling amount of a hydroxyaromatic poly(oxyalkylene) ether of the present invention.

The present invention additionally provides a fuel concentrate comprising an inert stable oleophilic organic solvent boiling in the range of from about 150° F. to 400° F. and from about 10 to 70 weight percent of a hydroxyaromatic poly(oxyalkylene) ether of the present invention.

Among other factors, the present invention is based on the surprising discovery that certain poly(oxyalkylene)

hydroxyaromatic ethers, when employed as fuel additives in fuel compositions, provide excellent control of engine deposits, especially on intake valves, and produce fewer combustion chamber deposits than known aliphatic hydrocarbon-substituted phenolic fuel additives.

DETAILED DESCRIPTION OF THE INVENTION

The fuel additives provided by the present invention have the general formula:

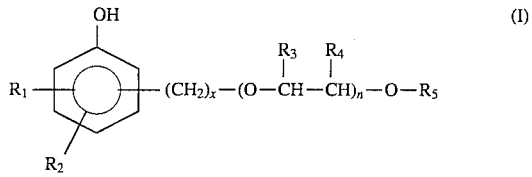

or a fuel-soluble salt thereof; wherein $R_1$, $R_2$, $R_3$, $R_4$, $R_5$, n and x are as defined hereinabove.

Preferably, $R_1$ is hydrogen, hydroxy, or lower alkyl having 1 to 4 carbon atoms. More preferably, $R_1$ is hydrogen or hydroxy. Most preferably, $R_1$ is hydrogen.

$R_2$ is preferably hydrogen.

Preferably, one of $R_3$ and $R_4$ is lower alkyl having 1 to 3 carbon atoms and the other is hydrogen. More preferably, one of $R_3$ and $R_4$ is methyl or ethyl and the other is hydrogen. Most preferably, one of $R_3$ and $R_4$ is ethyl and the other is hydrogen.

$R_5$ is preferably hydrogen, alkyl having 2 to 22 carbon atoms, alkylphenyl having an alkyl group containing 4 to 24 carbon atoms, or an acyl group having the formula: —$C(O)R_7$, wherein $R_7$ is alkyl having 4 to 12 carbon atoms. More preferably, $R_5$ is hydrogen, alkyl having 4 to 12 carbon atoms, or alkylphenyl having an alkyl group containing 4 to 12 carbon atoms. Most preferably, $R_5$ is hydrogen.

Preferably, n is an integer from 10 to 50. More preferably, n is an integer from 15 to 30. Preferably, x is an integer from 0 to 2. More preferably, x is 0.

A preferred group of poly(oxyalkylene) hydroxyaromatic ethers are those of formula I wherein $R_1$ is hydrogen, hydroxy, or lower alkyl having 1 to 4 carbon atoms; $R_2$ is hydrogen; one of $R_3$ and $R_4$ is hydrogen and the other is methyl or ethyl; $R_5$ is hydrogen, alkyl having 4 to 12 carbon atoms, alkylphenyl having an alkyl group containing 4 to 12 carbon atoms, or an acyl group having the formula: —$C(O)R_7$, wherein $R_7$ is alkyl having 4 to 12 carbon atoms; n is 15 to 30 and x is 0.

Another preferred group of poly(oxyalkylene) hydroxyaromatic ethers are those of formula I wherein $R_1$ is hydrogen, hydroxy, or lower alkyl having 1 to 4 carbon atoms; $R_2$ is hydrogen; one of $R_3$ and $R_4$ is hydrogen and the other is methyl or ethyl; $R_5$ is hydrogen, alkyl having 4 to 12 carbon atoms, alkylphenyl having an alkyl group containing 4 to 12 carbon atoms, or an acyl group having the formula: —$C(O)R_7$, wherein $R_7$ is alkyl having 4 to 12 carbon atoms; n is 15 to 30 and x is 1 or 2.

A more preferred group of poly(oxyalkylene) hydroxyaromatic ethers are those of formula I wherein $R_1$ is hydrogen or hydroxy; $R_2$ is hydrogen; one of $R_3$ and $R_4$ is hydrogen and the other is methyl or ethyl; $R_5$ is hydrogen, alkyl having 4 to 12 carbon atoms, or alkylphenyl having an alkyl group containing 4 to 12 carbon atoms; n is 15 to 30; and x is 0.

A particularly preferred group of poly(oxyalkylene) hydroxyaromatic ethers are those having the formula:

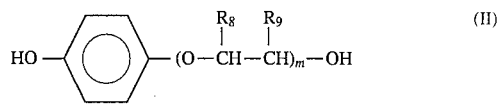

wherein one of $R_8$ and $R_9$ is methyl or ethyl and the other is hydrogen; and m is an integer from 15 to 30.

The poly(oxyalkylene) hydroxyaromatic ethers of the present invention will generally have a sufficient molecular weight so as to be non-volatile at normal engine intake valve operating temperatures (about 200°–250° C.). Typically, the molecular weight of the poly(oxyalkylene) hydroxyaromatic ethers of this invention will range from about 600 to about 10,000, preferably from 1,000 to 3,000.

Generally, the poly(oxyalkylene) hydroxyaromatic ethers of this invention will contain an average of about 5 to about 100 oxyalkylene units; preferably, 10 to 50 oxyalkylene units; more preferably, 15 to 30 oxyalkylene units.

Fuel-soluble salts of the poly(oxyalkylene) hydroxyaromatic ethers of the present invention are also contemplated to be useful for preventing or controlling deposits. Such salts include alkali metal, alkaline earth metal, ammonium, substituted ammonium and sulfonium salts. Preferred metal salts are the alkali metal salts, particularly the sodium and potassium salts, and the substituted ammonium salts, particularly tetraalkyl-substituted ammonium salts, such as the tetrabutylammonium salts.

Definitions

As used herein the following terms have the following meanings unless expressly stated to the contrary.

The term "alkyl" refers to both straight- and branched-chain alkyl groups.

The term "lower alkyl" refers to alkyl groups having 1 to about 6 carbon atoms and includes primary, secondary and tertiary alkyl groups. Typical lower alkyl groups include, for example, methyl, ethyl, n-propyl, isopropyl, n-butyl, sec-butyl, t-butyl, n-pentyl, n-hexyl and the like.

The term "lower alkoxy" refers to the group —$OR_a$ wherein $R_a$ is lower alkyl. Typical lower alkoxy groups include methoxy, ethoxy, and the like.

The term "alkaryl" refers to the group:

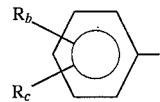

wherein $R_b$ and $R_c$ are each independently hydrogen or an alkyl group, with the proviso that both $R_b$ and $R_c$ are not hydrogen. Typical alkaryl groups include, for example, tolyl, xylyl, cumenyl, ethylphenyl, butylphenyl, dibutylphenyl, hexylphenyl, octylphenyl, dioctylphenyl, nonylphenyl, decylphenyl, didecylphenyl, dodecylphenyl, hexadecylphenyl, octadecylphenyl, icosylphenyl, tricontylphenyl and the like. The term "alkylphenyl" refers to an alkaryl group of the above formula in which $R_b$ is alkyl and $R_c$ is hydrogen.

The term "aralkyl" refers to the group:

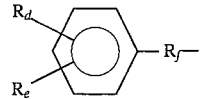

wherein $R_d$ and $R_e$ are each independently hydrogen or an alkyl group; and $R_f$ is an alkylene group. Typical alkaryl groups include, for example, benzyl, methylbenzyl, dimethylbenzyl, phenethyl, and the like.

The term "oxyalkylene unit" refers to an ether moiety having the general formula:

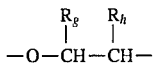

wherein $R_g$ and $R_h$ are each independently hydrogen or lower alkyl groups.

The term "poly(oxyalkylene)" refers to a polymer or oligomer having the general formula:

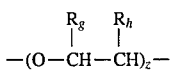

wherein $R_g$ and $R_h$ are as defined above, and z is an integer greater than 1. When referring herein to the number of poly(oxyalkylene) units in a particular poly(oxyalkylene) compound, it is to be understood that this number refers to the average number of poly(oxyalkylene) units in such compounds unless expressly stated to the contrary.

General Synthetic Procedures

The poly(oxyalkylene) hydroxyaromatic ethers of this invention may be prepared by the following general methods and procedures. It should be appreciated that where typical or preferred process conditions (e.g. reaction temperatures, times, mole ratios of reactants, solvents, pressures, etc.) are given, other process conditions may also be used unless otherwise stated. Optimum reaction conditions may vary with the particular reactants or solvents used, but such conditions can be determined by one skilled in the art by routine optimization procedures.

The poly(oxyalkylene) hydroxyaromatic ethers of the present invention may be prepared from a hydroxyaromatic compound having the formula:

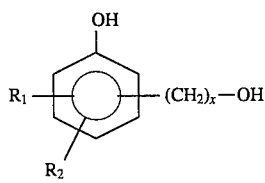

wherein $R_1$, $R_2$, and x are as defined above.

The hydroxyaromatic compounds of formula III are either known compounds or can be prepared from known compounds by conventional procedures. Suitable hydroxyaromatic compounds for use as starting materials in this invention include catechol, resorcinol, hydroquinone, 1,2,3-trihydroxybenzene (pyrogallol), 1,2,4-trihydroxybenzene (hydroquinol), 1,3,5-trihydroxybenzene (phloroglucinol), 1,4-dihydroxy-2-methylbenzene, 1,3-dihydroxy-5-methylbenzene, 2-t-butyl-1,4-dihydroxybenzene, 2,6-di-t-butyl-1, 4-dihydroxybenzene, 1,4-dihydroxy- 2-methoxybenzene, 1,3-dihydroxy-5-methoxybenzene, 4-hydroxybenzyl alcohol, 4-hydroxyphenethyl alcohol and the like.

In a preferred method of synthesizing the poly(oxyalkylene) hydroxyaromatic ethers of the present invention, a hydroxyaromatic compound of formula III is first selectively protected to provide a compound having the formula:

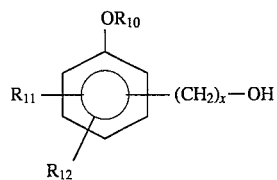

wherein $R_{10}$ is a suitable hydroxyl protecting group, such as benzyl, tert-butyldimethylsilyl, methoxymethyl, and the like; $R_{11}$ and $R_{12}$ are each independently hydrogen, lower alkyl, lower alkoxy, or the group —$OR_{13}$, wherein $R_{13}$ is a suitable hydroxyl protecting group, such as benzyl, tert-butyldimethylsilyl, methoxymethyl, and the like. Preferably, $R_{10}$ and $R_{13}$ are benzyl; except in the case where x is 1, then $R_{10}$ and $R_{13}$ are preferably a tert-butyl-dimethylsilyl group.

Selective protection of III may be accomplished using conventional procedures. The choice of a suitable protecting group for a particular hydroxyaromatic compound will be apparent to those skilled in the art. Various protecting groups, and their introduction and removal, are described, for example, in T. W. Greene and P. G. M. Wuts, *Protective Groups in Organic Synthesis*, Second Edition, Wiley, New York, 1991, and references cited therein. Alternatively, the protected derivatives IV can be prepared from known starting materials other than the hydroxyaromatic compounds of formula III by conventional procedures. In some cases, the protected derivatives IV are commercially available, e.g. 4-benzyloxyphenol is commercially available from Aldrich Chemical Co., Milwaukee, Wis. 53233.

The protected hydroxyaromatic compound of formula IV is then deprotonated with a suitable base to provide a metal salt having the formula:

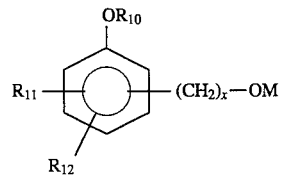

wherein $R_{10}$, $R_{11}$, $R_{12}$ and x are as defined above; and M is a metal cation, such as lithium, sodium or potassium.

Generally, this deprotonation reaction will be effected by contacting IV with a strong base, such as sodium hydride, potassium hydride, sodium amide and the like, in an inert solvent, such as toluene, xylene and the like, under substantially anhydrous conditions at a temperature in the range from about −10° C. to about 120° C. for about 0.25 to about 3 hours.

Metal salt V is generally not isolated, but is reacted in situ with about 5 to about 100 molar equivalents of an alkylene oxide (an epoxide) having the formula:

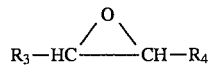

wherein $R_3$ and $R_4$ are as defined above, to provide, after neutralization, a poly(oxyalkylene) polymer or oligomer having the formula:

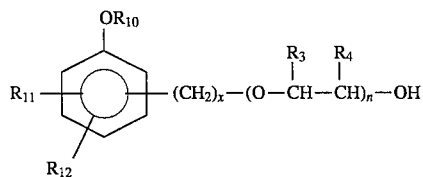

wherein $R_3$, $R_4$, $R_{10}$, $R_{11}$, $R_{12}$, n and x are as defined above.

Typically, this polymerization reaction is conducted in a substantially anhydrous inert solvent at a temperature of about 30° C. to about 150° C. for about 2 to about 120 hours. Suitable solvents for this reaction, include toluene, xylene and the like. The reaction will generally be conducted at a pressure sufficient to contain the reactants and the solvent, preferably at atmospheric or ambient pressure. More detailed reaction conditions for preparing poly(oxyalkylene) compounds may be found in U.S. Pat. Nos. 2,782,240 and 2,841,479, which are incorporated herein by reference.

The amount of alkylene oxide employed in this reaction will depend on the number of oxyalkylene units desired in the product. Typically, the molar ratio of alkylene oxide VI to metal salt V will range from about 5:1 to about 100:1; preferably, from 10:1 to 50:1, more preferably from 15:1 to 30:1.

Suitable alkylene oxides for use in the polymerization reaction include, for example, ethylene oxide; propylene oxide; butylene oxides, such as 1,2-butylene oxide (1,2-epoxybutane) and 2,3-butylene oxide (2,3-epoxybutane); pentylene oxides; hexylene oxides; octylene oxides and the like. Preferred alkylene oxides are propylene oxide and 1,2-butylene oxide.

In the polymerization reaction, a single type of alkylene oxide may be employed, e.g. propylene oxide, in which case the product is a homopolymer, e.g. a poly(oxypropylene). However, copolymers are equally satisfactory and random copolymers are readily prepared by contacting the metal salt V with a mixture of alkylene oxides, such as a mixture of propylene oxide and 1,2-butylene oxide, under polymerization conditions. Copolymers containing blocks of oxyalkylene units are also suitable for use in the present invention. Block copolymers may be prepared by contacting the metal salt V with first one alkylene oxide, then others in any order, or repetitively, under polymerization conditions.

Poly(oxyalkylene) polymers of formula VII may also be prepared by living or immortal polymerization as described by S. Inoue and T. Aida in *Encyclopedia of Polymer Science and Engineering*, Second Edition, Supplemental Volume, J. Wiley and Sons, New York, pages 412–420 (1989). These procedures are especially useful for preparing poly(oxyalkylene) alcohols of formula V in which $R_3$ and $R_4$ are both alkyl groups.

Deprotection of the aromatic hydroxyl group(s) of VII using conventional procedures provides poly(oxyalkylene) hydroxyaromatic ethers of the present invention having the formula:

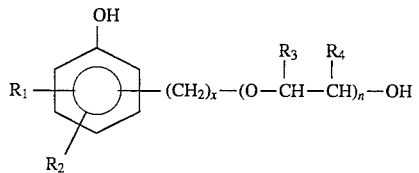

(VIII)

wherein $R_1$–$R_4$, n and x are as defined above.

Appropriate conditions for this deprotection step will depend upon the protecting group(s) utilized in the synthesis and will be readily apparent to those skilled in the art. For example, benzyl protecting groups may be removed by hydrogenolysis under 1 to about 4 atmospheres of hydrogen in the presence of a catalyst, such as palladium on carbon. Typically, this deprotection reaction will be conducted in an inert solvent, preferably a mixture of ethyl acetate and acetic acid, at a temperature of from about 0° C. to about 40° C. for about 1 to about 24 hours.

The poly(oxyalkylene) hydroxyaromatic ethers of the present invention containing an alkyl or alkaryl ether moiety, i.e. those having the formula:

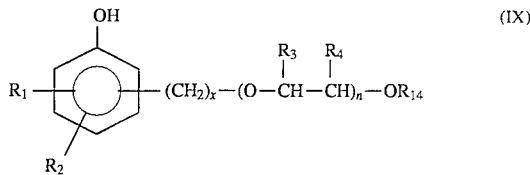

(IX)

wherein $R_1$–$R_4$, n and x are as defined above, and $R_{14}$ is an alkyl group or aralkyl group, may be conveniently prepared from a compound of formula VIII by selectively alkylating the hydroxyl group of the poly(oxyalkylene) moiety of VIII with a suitable alkylating agent.

Typically, this alkylation reaction will be conducted by first contacting VIII with a sufficient amount of a strong base capable of abstracting a proton from each the hydroxyl groups present in VIII, including the aromatic hydroxyl group(s) and the hydroxyl group of the poly(oxyalkylene) moiety. Suitable bases for this reaction include, for example, sodium hydride, potassium hydride, sodium amide and the like. Generally, this deprotonation reaction will be conducted in an inert solvent, such as toluene, tetrahydrofuran, and the like, under substantially anhydrous conditions at a temperature in the range from −10° C. to 120° C. for about 0.25 to about 3 hours. The resulting metal salt is then contacted with about 0.90 to about 1.1 molar equivalents of a suitable alkylating agent at a temperature in the range from 0° C. to 120° C. for about 1 to about 50 hours to afford, after neutralization, a poly(oxyalkylene) hydroxyaromatic ether of formula IX.

Suitable alkylating agents for use in this reaction include alkyl and aralkyl halides, such as alkyl chlorides, bromides and iodides and aralkyl chlorides, bromides and iodides; and alkyl and aralkyl sulfonates, such as alkyl mesylates and tosylates, and aralkyl mesylates and tosylates.

Preferred alkylating agents are primary and secondary alkyl halides having 1 to 30 carbon atoms, and primary and secondary aralkyl halides having 7 to 36 carbon atoms; more preferred alkylating agents are primary alkyl halides having 4 to 12 carbon atoms.

Representative examples of alkylating agents include, but are not limited to, methyl iodide, ethyl iodide, n-propyl bromide, n-butyl bromide, n-pentyl bromide, n-hexyl chloride, n-octyl chloride, n-decyl chloride, benzyl chloride and phenethyl chloride. Particularly preferred alkylating agents are benzyl chloride, n-butyl bromide.

Alternatively, poly(oxyalkylene) hydroxyaromatic ethers of formula IX may be prepared by alkylating the hydroxyl group of the poly(oxyalkylene) moiety of protected intermediate VII, and then deprotecting the resulting product. The conditions for alkylating intermediate VII are essentially the same as those described above; however, a lesser amount of base will be required since the aromatic hydroxyl groups of VII are in a protected form.

Other suitable methods for preparing alkyl and alkaryl ethers from alcohols, and appropriate reaction conditions for such reactions, can be found, for example, in I. T. Harrison and S. Harrison, *Compendium of Organic Synthetic Methods*, Vol. 1, pp. 310–312, Wiley-Interscience, New York (1971) and references cited therein.

The poly(oxyalkylene) hydroxyaromatic ethers of the present invention containing an alkaryl ether moiety, i.e. those having the formula:

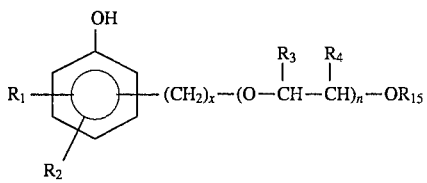

wherein $R_1$–$R_4$, n and x are as defined above, and $R_{15}$ is a phenyl or alkaryl group, may be prepared from intermediate VII in several steps by first converting the hydroxyl group present of the poly(oxyalkylene) moiety of VII into a suitable leaving group, i.e. forming an intermediate having the formula:

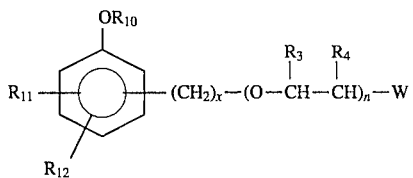

wherein $R_3$, $R_4$, $R_{10}$, $R_{11}$, $R_{12}$, n and x are as defined above, and W is a suitable leaving group; and then displacing the leaving group of XI with a metal salt of a phenol having the formula:

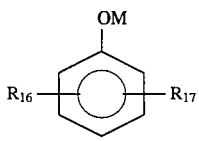

wherein $R_{16}$ and $R_{17}$ are each independently hydrogen or an alkyl group. Subsequent deprotection of the resulting product affords poly(oxyalkylene) hydroxyaromatic ethers of formula X.

The hydroxyl group of the poly(oxyalkylene) moiety of VII may be converted into a suitable leaving group by contacting VII with a sulfonyl chloride to form a sulfonate ester, such as a methanesulfonate (mesylate) or a toluenesulfonate (tosylate). Typically, this reaction is conducted in the presence of a suitable amine, such as triethylamine or pyridine, in an inert solvent, such as dichloromethane, at a temperature in the range of about −10° C. to about 30° C.

Alternatively, the hydroxyl group of the poly(oxyalkylene) moiety of VII can be exchanged for a halide, such as chloride or bromide, by contacting VII with a halogenating agent, such as thionyl chloride, oxalyl chloride or phosphorus tribromide. Other suitable methods for preparing sulfonates and halides from alcohols, and appropriate reaction conditions for such reactions, can be found, for example, in I. T. Harrison and S. Harrison, *Compendium of Organic Synthetic Methods*, Vol. 1, pp. 331–337, Wiley-Interscience, New York (1971) and references cited therein.

After forming intermediate XI, the leaving group may be displaced therefrom by contacting XI with metal salt XII. Generally, this reaction will be conducted in an inert solvent, such as toluene, tetrahydrofuran and the like, under substantially anhydrous conditions at a temperature in the range of about 25° C. to about 150° C. for about 1 to about 48 hours. The metal salt XII can be formed by contacting the corresponding phenol with a strong base capable of abstracting the proton from the phenolic hydroxyl group, such as sodium hydride, potassium hydride, sodium amide and the like, in an inert solvent.

Suitable phenolic compounds for use in this reaction include phenol, monoalkyl-substituted phenols and dialkyl-substituted phenols. Monoalkyl-substituted phenols are preferred, especially monoalkylphenols having an alkyl substituent in the para position. Representative examples of suitable phenolic compounds include, but are not limited to, phenol, methylphenol, dimethylphenol, ethylphenol, butylphenol, octylphenol, decylphenol, dodecylphenol, tetradecylphenol, hexadecylphenol, octadecylphenol, eicosylphenol, tetracosylphenol, hexacosylphenol, triacontylphenol and the like. Also, mixtures of alkylphenols may be employed, such as a mixture of $C_{14}$–$C_{18}$ alkylphenols, a mixture of $C_{18}$–$C_{24}$ alkylphenols, a mixture of $C_{20}$–$C_{24}$ alkylphenols, or a mixture of $C_{16}$–$C_{26}$ alkylphenols.

Particularly preferred alkylphenols are those derived from alkylation of phenol with polymers or oligomers of $C_3$ to $C_6$ olefins, such as polypropylene or polybutene. These polymers preferably contain 10 to 30 carbon atoms. An especially preferred alkylphenol is prepared by alkylating phenol with a propylene polymer having an average of 4 units. This polymer has the common name of propylene tetramer and is commercially available.

Alternatively, the poly(oxyalkylene) hydroxyaromatic ethers of formula X can be prepared by displacing a leaving group from an intermediate having the formula:

wherein $R_3$, $R_4$, $R_{15}$, n and x are as defined above, and W is a suitable leaving group, with metal salt V; and then deprotecting the resulting product. Conditions for this reaction are essentially the same as those described above for reaction of XI with XII. Compounds of formula XIII may be prepared from XII and VI using the conditions described above for the preparation of VII, followed by conversion of the hydroxyl group of the poly(oxyalkylene) moiety of the resulting product into a suitable leaving using the procedures described above for the preparation of XI.

The poly(oxyalkylene) hydroxyaromatic ethers of the present invention containing an acyl moiety, i.e those having the formula:

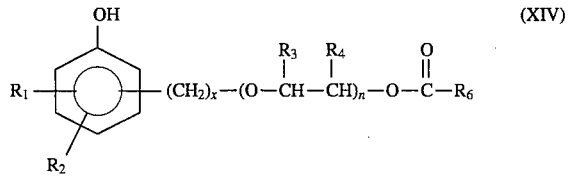

wherein $R_1$–$R_4$, $R_6$, n and x are as defined above; may be prepared from intermediate VII by first acylating the hydroxyl group of the poly(oxyalkylene) moiety of VII to form an ester. Subsequent deprotection of the aromatic hydroxyl group(s) of the resulting ester using conventional procedures then affords poly(oxyalkylene) hydroxyaromatic ethers of formula XIV.

Generally, the acylation reaction will be conducted by contacting intermediate VII with about 0.95 to about 1.2 molar equivalents of a suitable acylating agent. Suitable acylating agents for use in this reaction include acyl halides, such as acyl chlorides and bromides; and carboxylic acid anhydrides. Preferred acylating agents are those having the formula: $R_6C(O)$–X, wherein $R_6$ is alkyl having 1 to 30 carbon atom, phenyl, or aralkyl or alkaryl having 7 to 36 carbon atoms, and X is chloro or bromo. More preferred acylating agents are those having the formula: $R_7C(O)$–X, wherein $R_7$ is alkyl having 4 to 12 carbon atoms. Representative examples of suitable acylating agents include, but are not limited to, acetyl chloride, acetic anhydride, propionyl chloride, butanoyl chloride, pivaloyl chloride, octanoyl chloride, decanoyl chloride 4-t-butylbenzoyl chloride and the like.

Generally, this reaction is conducted in an inert solvent, such as toluene, dichloromethane, diethyl ether and the like, at a temperature in the range of about 25° C. to about 150° C., and is generally complete in about 0.5 to about 48 hours. When an acyl halide is employed as the acylating agent, this reaction is preferably conducted in the presence of a sufficient amount of an amine capable of neutralizing the acid generated during the reaction, such as triethylamine, di(isopropyl)ethylamine, pyridine or 4-dimethylaminopyridine.

Additional methods for preparing esters from alcohols, and suitable reaction conditions for such reactions, can be found, for example, in I. T. Harrison and S. Harrison, *Compendium of Organic Synthetic Methods*, Vol. 1, pp. 273–276 and 280–283, Wiley-Interscience, New York (1971) and references cited therein.

Fuel Compositions

The poly(oxyalkylene) hydroxyaromatic ethers of the present invention are useful as additives in hydrocarbon fuels to prevent and control engine deposits, particularly intake valve deposits. The proper concentration of additive necessary to achieve the desired deposit control varies depending upon the type of fuel employed, the type of engine, and the presence of other fuel additives.

In general, the concentration of the poly(oxyalkylene) hydroxyaromatic ethers of this invention in hydrocarbon fuel will range from about 50 to about 2500 parts per million (ppm) by weight, preferably from 75 to 1,000 ppm. When other deposit control additives are present, a lesser amount of the present additive may be used.

The poly(oxyalkylene) hydroxyaromatic ethers of the present invention may be formulated as a concentrate using an inert stable oleophilic (i.e., dissolves in gasoline) organic solvent boiling in the range of about 150° F. to 400° F. (about 65° C. to 205° C.). Preferably, an aliphatic or an aromatic hydrocarbon solvent is used, such as benzene, toluene, xylene or higher-boiling aromatics or aromatic thinners. Aliphatic alcohols containing about 3 to 8 carbon atoms, such as isopropanol, isobutylcarbinol, n-butanol and the like, in combination with hydrocarbon solvents are also suitable for use with the present additives. In the concentrate, the amount of the additive will generally range from about 10 to about 70 weight percent, preferably 10 to 50 weight percent, more preferably from 20 to 40 weight percent.

In gasoline fuels, other fuel additives may be employed with the additives of the present invention, including, for example, oxygenates, such as t-butyl methyl ether, antiknock agents, such as methylcyclopentadienyl manganese tricarbonyl, and other dispersants/detergents, such as hydrocarbyl amines, hydrocarbyl poly(oxyalkylene) amines, or succinimides. Additionally, antioxidants, metal deactivators and demulsifiers may be present.

In diesel fuels, other well-known additives can be employed, such as pour point depressants, flow improvers, cetane improvers, and the like.

A fuel-soluble, nonvolatile carrier fluid or oil may also be used with the poly(oxyalkylene) hydroxyaromatic ethers of this invention. The carrier fluid is a chemically inert hydrocarbon-soluble liquid vehicle which substantially increases the nonvolatile residue (NVR), or solvent-free liquid fraction of the fuel additive composition while not overwhelmingly contributing to octane requirement increase. The carrier fluid may be a natural or synthetic oil, such as mineral oil, refined petroleum oils, synthetic polyalkanes and alkenes, including hydrogenated and unhydrogenated polyalphaolefins, and synthetic polyoxyalkylene-derived oils, such as those described, for example, in U.S. Pat. No. 4,191,537 to Lewis.

These carrier fluids are believed to act as a carrier for the fuel additives of the present invention and to assist in removing and retarding deposits. The carrier fluid may also exhibit synergistic deposit control properties when used in combination with the poly(oxyalkylene) hydroxyaromatic ethers of this invention.

The carrier fluids are typically employed in amounts ranging from about 100 to about 5000 ppm by weight of the hydrocarbon fuel, preferably from 400 to 3000 ppm of the fuel. Preferably, the ratio of carrier fluid to deposit control additive will range from about 0.5:1 to about 10:1, more preferably from 1:1 to 4:1, most preferably about 2:1.

When employed in a fuel concentrate, carrier fluids will generally be present in amounts ranging from about 20 to about 60 weight percent, preferably from 30 to 50 weight percent.

EXAMPLES

The following examples are presented to illustrate specific embodiments of the present invention and synthetic preparations thereof; and should not be interpreted as limitations upon the scope of the invention.

Example 1

Preparation of
α-(4-Benzyloxyphenyl)-ω-hydroxypoly(oxybutylene)

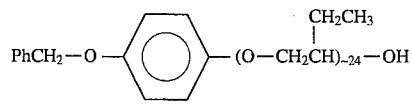

To a flask equipped with a magnetic stirrer, thermometer, addition funnel, reflux condenser and nitrogen inlet was added 6.88 grams of a 35 wt % dispersion of potassium hydride in mineral oil. Forty grams of 4-benzyloxyphenol dissolved in 500 mL of anhydrous toluene was added dropwise and the resulting mixture was stirred at room temperature for ten minutes. The temperature of the reaction mixture, a thick white suspension, was raised to 90° C. and 430.8 mL of 1,2-epoxybutane was added dropwise. The reaction mixture was refluxed until the pot temperature reached 110° C. (approximately 48 hours) at which time the reaction mixture was a light brown clear solution. The reaction was cooled to room temperature, quenched with 50 mL of methanol and diluted with 1 liter of diethyl ether. The resulting mixture was washed with saturated aqueous ammonium chloride, followed by water and saturated aqueous sodium chloride. The organic layer was dried over anhydrous magnesium sulfate, filtered and the solvents removed in vacuo to yield 390 grams of a yellow oil. The oil was chromatographed on silica gel, eluting with hexane: diethyl ether (1:1), to yield 339.3 grams of the desired product as a colorless oil.

Example 2

Preparation of α-(4-Hydroxyphenyl)-ω-hydroxypoly(oxybutylene)

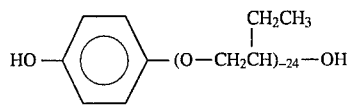

A solution of 54.10 grams of the product from Example 1 in 100 mL of ethyl acetate and 100 mL of acetic acid containing 5.86 grams of 10% palladium on charcoal was hydrogenolyzed at 35–40 psi for 16 hours on a Parr low-pressure hydrogenator. Catalyst filtration and removal of solvent in vacuo followed by azeotropic removal of residual acetic acid with toluene under vacuum yielded 48.1 grams of the desired product as a colorless oil. The product had an average of 24 oxybutylene units. $^1$H NMR (CDCl$_1$) δ 7.2 (broad s, 2H), 6.7 (s, 4H), 3.1–4.0 (m, 72H), 1.2–1.8 (m, 48H), 0.8 (t, 72H).

Similarly, by using the above procedures and the appropriate starting materials and reagents, the following compounds can by prepared:

α- (2-hydroxyphenyl)-ω-hydroxypoly(oxybutylene);

α-(3-hydroxyphenyl)-ω-hydroxypoly(oxybutylene);

α-(3-t-butyl-4-hydroxyphenyl)-ω-hydroxypoly(oxybutylene);

α-(4-hydroxy-3-methoxyphenyl)-ω-hydroxypoly(oxybutylene);

α-(3,4-dihydroxyphenyl)-ω-hydroxypoly(oxybutylene);

α-(3,4-hydroxy-5-methylphenyl)-ω-hydroxypoly(oxybutylene);

α-(3,5-di-t-butyl-4-hydroxyphenyl)-ω-hydroxypoly-(oxybutylene); and

α-(3,4,5-trihydroxyphenyl)-ω-hydroxypoly(oxybutylene).

Example 3

Preparation of α-(4-Benzyloxyphenyl)-ω-hydroxypoly(oxypropylene)

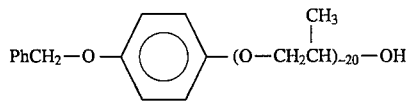

To a flask equipped with magnetic stirrer, thermometer, addition funnel, reflux condenser and nitrogen inlet was added 6.88 grams of a 35 wt % dispersion of potassium hydride in mineral oil. 4-Benzyloxyphenol (40 grams) dissolved in 500 mL of anhydrous toluene was added dropwise and then stirred at room temperature for ten minutes. The temperature of the reaction mixture, a thick white suspension, was raised to 110° C. and stirred for 3 hours. The reaction was cooled to room temperature and 349.9 mL of 1,2-epoxypropane was added dropwise. The reaction mixture was refluxed until the pot temperature reached 110° C. (approximately 96 hours) at which time the reaction mixture was a light brown clear solution. The reaction was cooled to room temperature, quenched with 50 mL of methanol and diluted with 1 liter of diethyl ether. The reaction was washed with saturated aqueous ammonium chloride, followed by water and saturated aqueous sodium chloride. The organic layer was dried over anhydrous sulfate, filtered and the solvents removed under vacuum to yield 212.2 grams of the desired product as a light yellow oil.

Example 4

Preparation of α-(4-Hydroxyphenyl)-ω-hydroxypoly(oxypropylene)

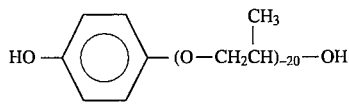

A solution of 60.0 grams of the product from Example 3 in 100 mL of ethyl acetate and 100 mL of acetic acid containing 7.0 grams of 10% palladium on charcoal was hydrogenolyzed at 35–40 psi for 16 hours on a Parr low-pressure hydrogenator. Catalyst filtration and removal of solvent in vacuo followed by azeotropic removal of the residual acetic acid with toluene under vacuum yielded 31.7 grams of the desired product as a brown oil. The product had an average of 20 oxypropylene units. $^1$H NMR (CDCl$_3$) δ 6.7 (s, 4H), 5.4–6.0 (broad s, 2H), 3.0–4.0 (m, 60H), 0.8–1.4 (m, 60H). Similarly, by using the above procedures and the appropriate starting materials and reagents, the following compounds can by prepared:

α-(2-hydroxyphenyl)-ω-hydroxypoly(oxypropylene);

α-(3-hydroxyphenyl)-ω-hydroxypoly(oxypropylene);

α-(4-hydroxy-3-methylphenyl)-ω-hydroxypoly(oxypropylene);

α-(3,5-dimethoxy-4-hydroxyphenyl)-ω-hydroxypoly(oxypropylene);

α-(3,4-dihydroxyphenyl)-ω-hydroxypoly(oxypropylene);

α-(3,5-di-t-butyl-4-hydroxyphenyl)-ω-hydroxypoly(oxypropylene); and

α-(3,4,5-trihydroxyphenyl)-ω-hydroxypoly(oxypropylene).

Example 5

Preparation of 2-(4-Benzyloxyphenyl)ethanol

To a flask equipped with a magnetic stirrer, reflux condenser and nitrogen inlet was added 13.8 grams of 2-(4-hydroxphenyl)ethanol, 14.5 grams of anhydrous potassium carbonate, 33.0 grams of tetrabutylammonium bromide, 12 mL of benzyl chloride and 200 mL of acetone. The reaction mixture was heated at reflux for 3 days, and then cooled to room temperature and filtered. The filtrate was concentrated in vacuo, diluted with 500 mL of dichloromethane, and washed with 2% aqueous sodium hydroxide and then with saturated brine. The organic layer was dried over anhydrous magnesium sulfate, filtered, and concentrated in vacuo. The resulting product was purified by chromatography on silica gel, eluting with dichloromethane, to yield 20.0 grams of the desired product as a white solid.

Example 6

Preparation of
α-[2-(4-Benzyloxyphenyl)ethyl]-ω-hydroxypoly
(oxybutylene)

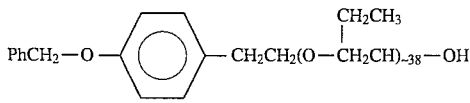

To a flask equipped with a magnetic stirrer, thermometer, addition funnel, reflux condenser and nitrogen inlet was added 1.05 grams of a 35 weight percent dispersion of potassium hydride in mineral oil and 50 mL of toluene. 2-(4-Benzyloxyphenyl)ethanol (6.8 grams) from Example 5, dissolved in 7.5 mL of toluene, was added dropwise and the mixture was heated at reflux for two hours. The reaction was cooled to room temperature and 65 mL of 1,2-epoxybutane were added dropwise. The reaction mixture was then refluxed until the pot temperature reached 110° C. (approximately 16 hours). The reaction was then cooled to room temperature, quenched with 50 mL of methanol and diluted with diethyl ether (300 mL). The organic layer was washed with water (2 times), saturated aqueous ammonium chloride (2 times), dried over anhydrous magnesium sulfate, filtered and concentrated in vacuo. The resulting product was chromatographed on silica gel, eluting with hexane/diethyl ether, followed by hexane/diethyl ether/ethanol (7.5:2.5:0.5) to yield 26.0 grams of the desired product as a colorless oil.

Example 7

Preparation of
α-[2-(4-Hydroxyphenyl)ethyl]-ω-hydroxypoly
(oxybutylene)

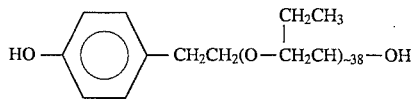

A solution of 26.0 grams of the product from Example 6 in 50 mL of ethyl acetate and 50 mL of acetic acid containing 3.0 grams of 10% palladium on charcoal was hydrogenolyzed at 35–40 psi for 16 hours on a Parr low-pressure hydrogenator. Catalyst filtration and removal of solvent in vacuo followed by azeotropic removal of residual acetic acid with toluene under vacuum yielded 21.0 grams of the desired product as a light yellow oil. The product had an average of 38 oxybutylene units. $^1$H NMR (CDCl$_3$) δ 6.7, 6.9 (AB quartet, 4H), 3.0–3.8 (m, 116H), 2.75 (t, 2H), 0.6–1.8 (m, 190H).

Similarly, by using the above procedures and the appropriate starting materials and reagents, the following compounds can by prepared:

α-[2-(2-hydroxyphenyl)ethyl]-ω-hydroxypoly(oxybutylene);

α-[2-(3-hydroxyphenyl)ethyl]-ω-hydroxypoly(oxybutylene);

α-[3-(4-hydroxyphenyl)propyl]-ω-hydroxypoly(oxybutylene);

α-[2-(3,4-dihydroxyphenyl)ethyl]-ω-hydroxypoly(oxybutylene);

α-[3-(3,4-dihydroxyphenyl)propyl]-ω-hydroxy-poly(oxybutylene);

α-[2-(3,5-di-t-butyl-4-hydroxyphenyl)ethyl]-ω-hydroxypoly(oxybutylene); and

α-[2-(3,4,5-trihydroxyphenyl)ethyl]-ω-hydroxypoly(oxybutylene).

Example 8

Preparation of
α-(4-Hydroxyphenyl)-ω-benzyloxypoly(oxybutylene)

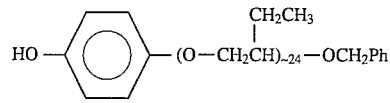

To a flask equipped with a magnetic stirrer, thermometer, reflux condenser and nitrogen inlet was added 0.8 grams of a 35 wt % dispersion of potassium hydride in mineral oil. The oil was removed by trituration with anhydrous toluene. The product from Example 2 (6.0 grams) was dissolved in 50 mL of anhydrous tetrahydrofuran and added dropwise to the potassium hydride. The reaction mixture was heated to reflux for 45 minutes and then cooled to room temperature. Benzyl chloride (0.36 mL) was added dropwise and the reaction was then heated to reflux for 12 hours, cooled to room temperature and quenched with 2 mL of isopropanol. The solvent was removed in vacuo and the residue dissolved in 200 mL of diethyl ether, washed with 5% aqueous hydrochloric acid followed by saturated aqueous sodium chloride. The organic layer was dried over anhydrous magnesium sulfate, filtered and the solvents removed under vacuum. The oil was chromatographed on silica gel, eluting with hexane/ethyl acetate (7:3), to yield 3.8 grams of the desired product as a colorless oil. The product had an average of 24 oxybutylene units. $^1$H NMR (CDCl$_3$) δ 7.2–7.4 (m, 6H), 6.7 (s, 4H), 4.4–4.7 (m, 2H), 3.1–4.0 (m, 72H), 1.2–1.8 (m, 48H), 0.8 (t, 72H).

Similarly, by using the above procedures and the appropriate starting materials and reagents, the following compounds can by prepared:

α-(2-hydroxyphenyl)-ω-benzyloxypoly(oxybutylene);

α-(3-hydroxyphenyl)-ω-benzyloxypoly(oxybutylene);

α-(3,4-dihydroxyphenyl)-ω-benzyloxypoly(oxybutylene);

α-(3,5-di-t-butyl-4-hydroxyphenyl)-ω-benzyloxypoly(oxybutylene);

α-(4-hydroxy-3-methoxyphenyl)-ω-benzyloxypoly(oxybutylene); and

α-(4-hydroxyphenyl)ethyl]-ω-benzyloxypoly(oxybutylene).

Example 9

Preparation of
α-(4-Benzoxyphenyl)-ω-docosanoxypoly(oxybutylene)

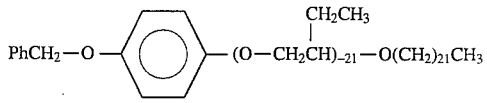

To a flask equipped with a magnetic stirrer, addition funnel, reflux condenser and nitrogen inlet was added 7.26 grams of a 35 wt % dispersion of potassium hydride in mineral oil. The oil was removed by trituration with anhydrous hexane, and 500 milliliters of anhydrous tetrahydrofuran were added. α-(4-Benzyloxyphenyl)-ω-hydroxypoly(oxybutylene) (104.0 grams) containing an average of 21 oxybutylene units (prepared essentially as described in Example 1), dissolved in 100 milliliters of anhydrous tetrahydrofuran, was added dropwise and the resulting mixture was heated to reflux for two hours. The reaction was then cooled to room temperature and 24.0 grams of 1-bromodocosane were added. The reaction was refluxed for sixteen hours, cooled to room temperature, diluted with 1200 mL of diethyl ether, and washed with 5% aqueous hydrochloric acid, followed by brine. The organic layers were dried over anhydrous magnesium sulfate, filtered and concentrated in vacuo to give an oil. The oil was chromatographed on silica gel, eluting with hexane/ethyl acetate (7:3) to yield 11.0 grams of the desired product as a yellow oil.

Example 10

Preparation of
α-(4-Hydroxyphenyl)-ω-docosanoxypoly(oxybutylene)

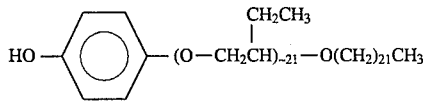

A solution of 11.0 grams of the product from Example 9 in 50 mL of ethyl acetate and 50 mL of acetic acid containing 1.5 grams of 10% palladium on charcoal was hydrogenolyzed at 35–40 psi for 14 hours on a Parr low-pressure hydrogenator. Catalyst filtration and removal of solvent in vacuo followed by azeotropic removal of the residual acetic acid with toluene under vacuum yielded 10.2 grams of the desired product. The product had an average of 21 oxybutylene units. $^1$H NMR (CDCl$_3$) δ 6.7 (s,4H), 3.1–4.0 (m, 62H), 0.6–1.8 (m, 148H).

Similarly, by using the above procedures and the appropriate starting materials and reagents, the following compounds can by prepared:

α-(4-hydroxyphenyl)-ω-n-butoxypoly(oxybutylene);

α-(4-hydroxyphenyl)-ω-n-octyloxypoly(oxybutylene);

α-(4-hydroxyphenyl)-ω-n-dodecyloxypoly(oxybutylene);

α-(3,5-di-t-butyl-4-hydroxyphenyl)-ω-n-pentyloxypoly(oxybutylene);

α-(4-hydroxy-3-methoxyphenyl)-ω-n-hexyloxypoly(oxybutylene);

α-(3,4-hydroxyphenyl)-ω-nonyloxypoly(oxybutylene); and

α-[2-(4-hydroxyphenyl)ethyl]-ω-octyloxypoly(oxybutylene).

Example 11

Preparation of
α-(Methanesulfonyl)-ω-4-dodecylphenoxypoly(oxybutylene)

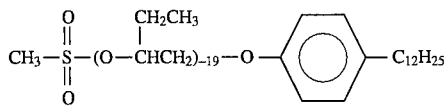

To a flask equipped with a magnetic stirrer, septa and a nitrogen inlet was added 35.0 grams of α-hydroxy-ω-4-dodecylphenoxypoly(oxybutylene) having an average of 19 oxybutylene units (prepared essentially as described in Example 6 of U.S. Pat. No. 4,160,648), 440 mL of dichloromethane and 3.6 mL of triethylamine. The flask was cooled in an ice bath and 1.8 mL of methanesulfonyl chloride were added dropwise. The ice bath was removed and the reaction was stirred at room temperature for 16 hours. Dichloromethane (800 mL) was added and the organic phase was washed two times with saturated aqueous sodium bicarbonate, and then once with brine. The organic layer was dried over anhydrous magnesium sulfate, filtered and concentrated in vacuo to yield 35.04 grams of the desired product as a yellow oil.

Example 12

Preparation of
α-(4-Benzyloxyphenyl)-ω-4-dodecylphenoxypoly(oxybutylene)

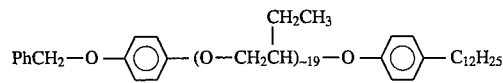

To a flask equipped magnetic stirrer, reflux condenser, nitrogen inlet and septa was added 2.59 grams of a 35 wt % dispersion of potassium hydride in mineral oil. The mineral oil was removed by trituration with hexane and the flask was cooled in an ice bath. 4-Benzyloxyphenol (4.11 grams) dissolved in 150 mL of tetrahydrofuran was added dropwise. The ice bath was removed and the reaction was allowed to stir for 45 minutes at room temperature. The mesylate from Example 11 was dissolved in 275 mL of anhydrous tetrahydrofuran and added to the reaction mixture. The resulting solution was refluxed for 16 hours, cooled to room temperature and 10 mL of methanol were added. The reaction was diluted with 1 liter of diethyl ether, washed with water (1 time), brine (1 time), dried over anhydrous magnesium sulfate, filtered and concentrated in vacuo to 36.04 grams of a yellow oil. The oil was chromatographed on silica gel, eluting with hexane/diethyl ether/ethanol (8:1.8:0.2) to yield 18.88 grams of the desired product as a light yellow oil.

Example 13

Preparation of
α-(4-Hydroxyphenyl)-ω-4-dodecylphenoxypoly(oxybutylene)

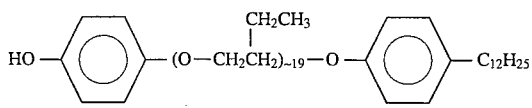

A solution of 18.88 grams of the product from Example 12 in 80 mL of ethyl acetate and 80 mL of acetic acid containing 2.08 grams of 10% palladium on charcoal was hydrogenolyzed at 35–40 psi for 6 hours on a Parr low-pressure hydrogenator. Filtration of the catalyst and removal of solvent in vacuo, followed by azeotropic removal of residual acetic acid with toluene under vacuum yielded 17.63 grams of the desired product as a yellow oil. The product had an average of 19 oxybutylene units. $^1$H NMR (CDCl$_3$) δ 7.0–7.3 (M, 2H), 6.6–6.9 (m, 6H), 4.0–4.2 (m, 1H), 3.8–4.0 (m, 2H), 3.0–3.8 (m, 54H), 0.5–1.8 (m, 120H).

Similarly, by using the above procedures and the appropriate starting materials and reagents, the following compounds can by prepared:

- α-(2-hydroxyphenyl)-ω-4-dodecylphenoxypoly(oxybutylene);
- α-(3-hydroxyphenyl)-ω-4-dodecylphenoxypoly(oxybutylene);
- α-(3,4-dihydroxyphenyl)-ω-4-dodecylphenoxypoly(oxybutylene);
- α-(4-hydroxyphenyl)-ω-phenoxypoly(oxybutylene);
- α-(4-hydroxyphenyl)-ω-4-t-butylphenoxypoly(oxybutylene);
- α-(4-hydroxyphenyl)-ω-4-decylphenoxypoly(oxybutylene); and
- α-(4-hydroxyphenyl)-ω-4-octadecylphenoxypoly(oxybutylene).

Example 14

Preparation of
α-(4-Benzoxyphenyl)-ω-decanoyloxypoly(oxybutylene)

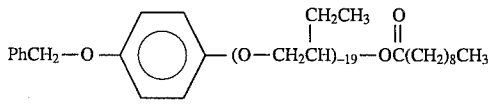

α-(4-Benzoxyphenyl)-ω-hydroxypoly(oxybutylene) (40.75 grams) containing an average of 19 oxybutylene units (prepared essentially as described in Example 1) was combined with 200 mL of toluene, 3.9 mL of triethylamine, 1.5 grams of 4-dimethylamine pyridine and 5.2 mL of n-decanoyl chloride in a flask equipped with a thermometer, magnetic stirrer, reflux condenser and nitrogen inlet. The contents were refluxed for 16 hours, cooled to room temperature and diluted with 400 mL of hexane. The organic layers were washed with water (2 times), saturated aqueous sodium bicarbonate (2 times), saturated aqueous sodium chloride (2 times), dried over anhydrous magnesium sulfate, filtered and concentrated to yield 40 grams of a yellow oil. The oil was chromatographed on silica gel, eluting with hexane/diethyl ether (1:1) to yield 23.3 grams of the product as a yellow oil.

Example 15

Preparation of
α-(4-Hydroxyphenyl)-ω-decanoyloxypoly(oxybutylene)

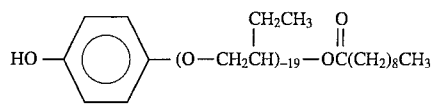

A solution of the ester from Example 14 (23.3 grams) in 50 mL of ethyl acetate and 50 mL of acetic acid containing 2.5 grams of 10% palladium on charcoal was hydrogenolyzed at 35–40 psi for 16 hours on a Parr low-pressure hydrogenator. Filtration of the catalyst and removal of solvent in vacuo followed by azeotropic removal of residual acetic acid with toluene under vacuum yielded 16.0 grams of the desired product as a yellow oil. The product had an average of 19 oxybutylene units. IR (neat) 1735 cm$^{-1}$; $^1$H NMR (CDCl$_3$) δ 6.7 (s, 4H), 4.8–4.9 (m, 1H), 3.1–4.0 (m, 56H), 2.3 (t, 2H), 0.7–1.8 (m, 112H).

Similarly, by using the above procedures and the appropriate starting materials and reagents, the following compounds can by prepared:

- α-(2-hydroxyphenyl)-ω-decanoyloxypoly(oxybutylene);
- α-(3-hydroxyphenyl)-ω-decanoyloxypoly(oxybutylene);
- α-(4-hydroxyphenyl)-ω-dodecanoyloxypoly(oxybutylene);
- α-(4-hydroxyphenyl)-ω-octanoyloxypoly(oxybutylene);
- α-(4-hydroxyphenyl)-ω-butanoyloxypoly(oxybutylene);
- α-(4-hydroxyphenyl)-ω-benzoyloxypoly(oxybutylene);
- α-(3,4-dihydroxyphenyl)-ω-hexanoyloxypoly(oxybutylene);
- α-(3,4-hydroxyphenyl)-ω-2-ethylhexanoyloxypoly(oxybutylene);
- α-(3,5-di-t-butyl-4-hydroxyphenyl)-ω-nonanoyloxypoly(oxybutylene);
- α-(3,4,5-trihydroxyphenyl)-ω-decanoyloxypoly(oxybutylene); and
- α-[2-(4-hydroxyphenyl)ethyl]-ω-decanoyloxypoly(oxybutylene).

Comparative Example A

Preparation of Polyisobutylphenol

To a flask equipped with a magnetic stirrer, reflux condenser, thermometer, addition funnel and nitrogen inlet was added 203.2 grams of phenol. The phenol was warmed to 40° C. and boron trifluoride etherate (73.5 mL) was added dropwise. Ultravis 10 polyisobutene (1040 grams, molecular weight 950, 76% methylvinylidene isomer, available from British Petroleum), dissolved in 1,863 mL of hexane, was then added to the reaction mixture at a rate sufficient to maintain the temperature between 22°–27° C. The reaction mixture was then stirred for 16 hours at room temperature. Concentrated ammonium hydroxide (400 mL) was then added and the mixture was diluted with 2 L of hexane. The resulting mixture was washed with water (3×2 L), dried over anhydrous magnesium sulfate, filtered and the solvent removed in vacuo to yield 1,056.5 grams of an oil. This oil was determined to contain 80% of the desired polyisobutylphenol and 20% polyisobutene by $^1$H NMR, and also by chromatography on silica gel, eluting first with hexane and then with hexane/ethyl acetate/ethanol (93:5:2).

Example 16

Single-Cylinder Engine Test

The test compounds were bended in gasoline and their deposit reducing capacity determined in an ASTM/CFR single-cylinder engine test.

A Waukesha CFR single-cylinder engine was used. Each run was carried out for 15 hours, at the end of which time the intake valve was removed, washed with hexane and weighed. The previously determined weight of the clean valve was subtracted from the weight of the value at the end of the run. The differences between the two weights is the weight of the deposit. A lesser amount of deposit indicates a superior additive. The operating conditions of the test were as follows: water jacket temperature 200° F.; vacuum of 12 in Hg, air-fuel ratio of 12, ignition spark timing of 40° BTC; engine speed is 1800 rpm; the crankcase oil is a commercial 30W oil.

The amount of carbonaceous deposit in milligrams on the intake valves is reported for each of the test compounds in Table I.

TABLE I

Single-Cylinder Engine Test Results

| Sample[1] | Intake Valve Deposit Weight (in milligrams) | | |
|---|---|---|---|
| | Run 1 | Run 2 | Average |
| Base Fuel | 214.7 | 193.7 | 204.2 |
| Example 2 | 12.7 | 26.5 | 19.6 |
| Example 4 | 59.6 | 73.8 | 66.7 |
| Example 7 | 44.3 | 54.0 | 42.9 |
| Example 8 | 52.8 | 75.9 | 64.4 |
| Example 10 | 53.9 | 47.9 | 50.9 |
| Example 13 | 32.2 | 32.3 | 32.3 |
| Example 15 | 32.5 | 31.1 | 31.8 |

[1]At 200 parts per million actives (ppma).

The base fuel employed in the above single-cylinder engine tests was a regular octane unleaded gasoline containing no fuel detergent. The test compounds were admixed with the base fuel to give a concentration of 200 ppma (parts per million actives).

The data in Table I illustrates the significant reduction in intake valve deposits provided by the poly(oxyalkylene) hydroxyaromatic ethers of the present invention (Examples 2, 4, 7, 8, 10, 13, 15) compared to the base fuel.

Example 17

Multicylinder Engine Test

The poly(oxyalkylene) hydroxyaromatic ethers of the present invention were tested in a laboratory multicylinder engine to evaluate their intake valve and combustion chamber deposit control performance. The test engine was a 4.3 liter, TBI (throttle body injected), V6 engine manufactured by General Motors Corporation.

The major engine dimensions are set forth in Table II:

TABLE II

| Engine Dimensions | |
|---|---|
| Bore | 10.16 cm |
| Stroke | 8.84 cm |
| Displacement Volume | 4.3 liter |
| Compression Ratio | 9.3:1 |

The test engine was operated for 40 hours (24 hours a day) on a prescribed load and speed schedule representative of typical driving conditions. The cycle for engine operation during the test is set forth in Table III.

TABLE III

Engine Driving Cycle

| Step | Mode | Time in Mode [Sec][1] | Dynamometer Load [kg] | Engine Speed [RPM] |
|---|---|---|---|---|
| 1 | Idle | 60 | 0 | 800 |
| 2 | City Cruise | 150 | 10 | 1,500 |
| 3 | Acceleration | 40 | 25 | 2,800 |
| 4 | Heavy HWY Cruise | 210 | 15 | 2,200 |
| 5 | Light HWY Cruise | 60 | 10 | 2,200 |
| 6 | Idle | 60 | 0 | 800 |
| 7 | City Cruise | 180 | 10 | 1,500 |
| 8 | Idle | 60 | 0 | 800 |

[1]All steps, except step number 3, include a 15 second transition ramp. Step 3 includes a 20 second transition ramp.

All of the test runs were made with the same base gasoline, which was representative of commercial unleaded fuel. The results are set forth in Table IV.

TABLE IV

Multicylinder Engine Test Results

| Sample[1] | | Intake Valve Deposits[2] | Combustion Chamber Deposits[2] |
|---|---|---|---|
| Base Fuel | Run 1 | 951 | 1887 |
| | Run 2 | 993 | 1916 |
| | Average | 972 | 1902 |
| Example 2 | Run 1 | 266 | 2571 |
| | Run 2 | 300 | 2522 |
| | Average | 283 | 2547 |
| Comparative | Run 1 | 229 | 2699 |
| Example A | Run 2 | 218 | 2738 |
| | Average | 224 | 2719 |

[1]At 400 parts per million actives (ppma).
[2]In milligrams (mg).

The base fuel employed in the above multicylinder engine tests contained no fuel detergent. The test compounds were admixed with the base fuel to give a concentration of 400 ppma (parts per million actives).

The data in Table IV illustrates the significant reduction in intake valve deposits provided by the poly(oxyalkylene) hydroxyaromatic ethers of the present invention (Example 2) compared to the base fuel. Moreover, the data in Table IV further demonstrates the significant reduction in combustion chamber deposits produced by the poly(oxyalkylene) hydroxyaromatic ethers of the present invention (Example 2) compared to a known polyisobutylphenol fuel additive (Comparative Example A).

What is claimed is:

1. A fuel composition comprising a major amount of hydrocarbons boiling in the gasoline or diesel range and an effective detergent amount of a compound of the formula:

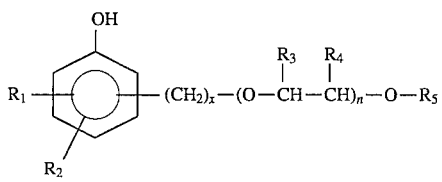

or a fuel-soluble salt thereof; wherein $R_1$ and $R_2$ are each independently hydrogen, hydroxy, lower alkyl having 1 to 6 carbon atoms, or lower alkoxy having 1 to 6 carbon atoms;

$R_3$ and $R_4$ are each independently hydrogen or lower alkyl having 1 to 6 carbon atoms;

$R_5$ is hydrogen, alkyl having 1 to 30 carbon atoms, phenyl, aralkyl or alkaryl having 7 to 36 carbon atoms, or an acyl group of the formula:

wherein $R_6$ is alkyl having 1 to 30 carbon atoms, phenyl, or aralkyl or alkaryl having 7 to 36 carbon atoms;

n is an integer from 5 to 100; and x is an integer from 0 to 10.

2. The fuel composition according to claim 1, wherein $R_1$ is hydrogen, hydroxy, or lower alkyl having 1 to 4 carbon atoms; $R_2$ is hydrogen; one of $R_3$ and $R_4$ is hydrogen and the other is methyl or ethyl; $R_5$ is hydrogen, alkyl having 2 to 22 carbon atoms, alkylphenyl having an alkyl group containing 4 to 24 carbon atoms, or an acyl group having the formula: —C(O)$R_7$, wherein $R_7$ is alkyl having 4 to 12 carbon atoms; n is 15 to 30 and x is 0, 1 or 2.

3. The fuel composition according to claim 2, wherein $R_1$ is hydrogen or hydroxy; $R_5$ is hydrogen, alkyl having 4 to 12 carbon atoms, or alkylphenyl having an alkyl group containing 4 to 12 carbon atoms; and x is 0.

4. The fuel composition according to claim 3, wherein $R_1$ and $R_5$ are both hydrogen.

5. The fuel composition according to claim 1, wherein said composition contains about 50 to about 2500 parts per million by weight of said compound.

6. The fuel composition according to claim 1, wherein n is an integer ranging from 10 to 50.

7. The fuel composition according to claim 6, wherein n is an integer ranging from 15 to 30.

8. The fuel composition according to claim 1, wherein $R_1$ is hydrogen, hydroxy, or lower alkyl having 1 to 4 carbon atoms; and $R_2$ is hydrogen.

9. The fuel composition according to claim 8, wherein $R_1$ is hydrogen or hydroxy.

10. The fuel composition according to claim 1, wherein $R_5$ is hydrogen, alkyl having 2 to 22 carbon atoms, alkylphenyl having an alkyl group containing 4 to 24 carbon atoms, or an acyl group having the formula: —C(O)$R_7$, wherein $R_7$ is alkyl having 4 to 12 carbon atoms.

11. The fuel composition according to claim 10, wherein $R_5$ is hydrogen, alkyl having 4 to 12 carbon atoms, or alkylphenyl having an alkyl group containing 4 to 12 carbon atoms.

12. The fuel composition according to claim 1, wherein one of $R_3$ and $R_4$ is lower alkyl having 1 to 3 carbon atoms and the other is hydrogen.

13. The fuel composition according to claim 12, wherein one of $R_3$ and $R_4$ is methyl or ethyl and the other is hydrogen.

14. The fuel composition according to claim 1, wherein x is 0, 1 or 2.

15. The fuel composition according to claim 14, wherein x is 0.

* * * * *